United States Patent [19]

Krishnan et al.

[11] Patent Number: 5,675,030

[45] Date of Patent: Oct. 7, 1997

[54] METHOD FOR SELECTIVE EXTRACTING A 7-(HYDROGEN OR SUBSTITUTED AMINO)-9-[(SUBSTITUTED GLYCYL) AMIDO]-6-DEMETHYL-6-DEOXYTETRACYCLINE COMPOUND

[75] Inventors: Lalitha Krishnan; Richard A. Leese; Raghavan Krishnan, all of Suffern, N.Y.

[73] Assignee: American Cyanamid Company, Madison, N.J.

[21] Appl. No.: 340,552

[22] Filed: Nov. 16, 1994

[51] Int. Cl.[6] ........................... A61K 31/65
[52] U.S. Cl. ................................. 552/205
[58] Field of Search ........................ 552/205

[56] References Cited

U.S. PATENT DOCUMENTS

| | | |
|---|---|---|
| Re. 26,253 | 8/1967 | Petisi et al. . |
| 3,226,436 | 12/1965 | Petisi et al. . |
| 3,518,306 | 6/1970 | Martell et al. . |
| 3,901,942 | 8/1975 | Bernardi et al. ............ 552/205 |
| 4,918,208 | 4/1990 | Hasegawa et al. ........... 552/205 |
| 5,248,797 | 9/1993 | Sum . |
| 5,401,729 | 3/1995 | Sum et al. ................. 552/205 |

OTHER PUBLICATIONS

Merck Index, 10th Edition, 1983, Entrees #2111 and 5936.
The Chemistry of the Tetracycline Antibiotics, L.A. Mitscher, pp. 52–54 and 172–173, 1960.

The Journal of the American Chemical Society, vol. 82, 1960, pp. 1253–1254.

Primary Examiner—Rebecca Cook
Attorney, Agent, or Firm—T. S. Szatkowski

[57] ABSTRACT

The invention provides a method for selectively extracting a compound of formula I:

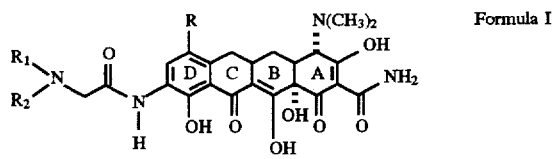

wherein: R is hydrogen or $-NR_3R_4$; and when $R=-NR_3R_4$, $R_3$ and $R_4$ may be the same or different and are selected from hydrogen and straight or branched ($C_1$–$C_4$) alkyl; $R_1$ and $R_2$ may be the same or different and are selected from straight or branched ($C_1$–$C_6$)alkyl; from an aqueous mixture containing a compound of Formula I, its C-4 epimer and its oxidative degradation by-products by adding methylene at a concentration of 2–4 ml of methylene chloride per gram of compound of Formula I and at a pH between pH 6.5–8.0; and obtaining an extract containing methylene chloride, a compound of Formula I, and its C-4 epimer, said epimer being present in an amount of less than 3% of the amount of the compound of Formula I.

14 Claims, No Drawings

METHOD FOR SELECTIVE EXTRACTING A 7-(HYDROGEN OR SUBSTITUTED AMINO)-9-[(SUBSTITUTED GLYCYL) AMIDO]-6-DEMETHYL-6-DEOXYTETRACYCLINE COMPOUND

BACKGROUND OF THE INVENTION

1. Field of the Invention

The invention is concerned with a method of purifying [4S-(4alpha,12aalpha)]-7-(hydrogen or substituted amino)-9-[(substituted glycyl)amido]-4-(dimethylamino)-1,4,4a,5,5a,6,11,12a-octahydro-3,10,12,12a-tetrahydroxy-1,11-dioxo-2-naphthacenecarboxamide, hereinafter called 7-(hydrogen or substituted amino)-9-[(substituted glycyl) amido]-6-demethyl-6-deoxytetracycline, from a mixture comprising the desired 7-(hydrogen or substituted amino)-9-[(substituted glycyl)amido]-6-demethyl-6-deoxytetracycline, the C-4 epimer thereof and the oxidative degradation by-products thereof by selectively extracting with methylene chloride.

2. Background of the Invention

The tetracycline molecule presents a special challenge to the synthetic organic chemist. The molecule is very readily oxidized at the C-11 and C-12a positions; and when there is a 7-disubstituted amino group, the D ring is an aminophenol which is prone to oxidation. All tetracyclines, to varying degrees, epimerize at the C-4 position of the D ring with resultant decrease in antibacterial activity. In *The Chemistry of the Tetracyline Antibiotic*, MARCEL DEKKER, INC., Chapter 6.3, p. 172–173 and Chapter 2, p. 53–54, 1978, L. A. Mitscher states that the natural α-orientation of the C-4 dimethylamino group is essential for bioactivity. Mitscher also states that epimerization results in loss of potency and 4-epianhydrotetracycline is toxic to the kidneys involving a Fanconi-like syndrome. Finally, L. A. Mitscher states that tetracyclines show relatively little tendency to extract at any pH into common water immiscible organic solvents such as diethyl ether and chloroform.

In order to avoid problems caused by epimerization, it becomes necessary to devise purification methods to lower the C-4 epimer content of 7-(hydrogen or substituted amino) -9-[(substituted glycyl)amido]-6-demethyl-6-deoxytetracycline materials. Since the 7-(hydrogen or substituted amino)-9-[(substituted glycyl)amido]-6-demethyl-6-deoxytetracyclines are amphoteric, behaving either as an acid or base, and possess functional groups that can chelate readily, many of the conventional purification techniques for organic compounds, such as chromatography on silica gel or preparative HPLC, cannot be applied to their purification. In the past, some tetracyclines were purified by partition chromatography using columns made of diatomaceous earth which were impregnated with buffered stationary phases containing sequestering agents such as EDTA. These purification columns have very low resolution, reproducibility and capacity and hence are not amenable to large-scale synthesis. Adaptation of the analytical HPLC systems to preparative systems has not been successful due largely to the pH dependence of the separations and to the fact that it becomes almost impossible to separate the final product from sequestering and ion-pairing agents in the mobile phase. In addition, purification by column chromatography is inefficient and impractical when dealing with kilogram quantities of material.

SUMMARY OF THE INVENTION

The invention provides a method for purifying a compound of formula I:

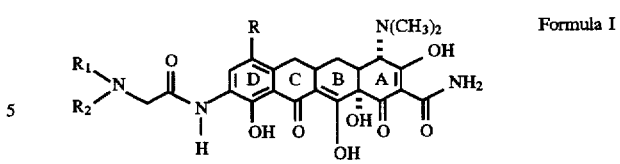

Formula I wherein: R is hydrogen or —NR$_3$R$_4$; and when R=—NR$_3$R$_4$, R$_3$ and R$_4$ may be the same or different and are selected from hydrogen and straight or branched (C$_1$–C$_4$) alkyl; R$_1$ and R$_2$ may be the same or different and are selected from straight or branched (C$_1$–C$_6$)alkyl; from an aqueous mixture containing a compound of Formula I, its C-4 epimer and its oxidative degradation by-products which method comprises selectively extracting the compound of Formula I from the aqueous mixture with methylene chloride at a concentration of 2–4 ml methylene chloride per gram of compound of Formula I and a pH between pH 6.5–8.0; and obtaining an extract of a compound of Formula I having less than 3% of the C-4 epimer.

The invention also provides for the conversion of a compound of Formula I so extracted to its corresponding pharmaceutically acceptable acid salt. The pharmaceutically acceptable salt of a 7-(hydrogen or substituted amino)-9-[(substituted glycyl)amido]-6-demethyl-6-deoxy tetracycline include inorganic salts such as hydrochloride, hydrobromide, hydroiodide, phosphate, nitrate, or sulfate; or organic salts such as acetate, benzoate, citrate, cysteine or other amino acids, fumarate, glycolate, maleate, succinate, tartrate, alkylsulfonate or arylfulfonate. It is known to one skilled in the art that an appropriate salt form is chosen based on physical and chemical stability, flowability, hygroscopicity and solubility. It is also known to those skilled in the art, that the above salts are made from the corresponding acid, so that hydrochloric acid gives the hydrochloride salt, sulfuric acid gives the sulfate salt, and acetic acid gives the acetate salt.

The invention thus contributes to the art a selective method for separating the desired 7-(hydrogen or substituted amino)-9-[(substituted glycyl)amido]-6-demethyl-6-deoxytetracycline:

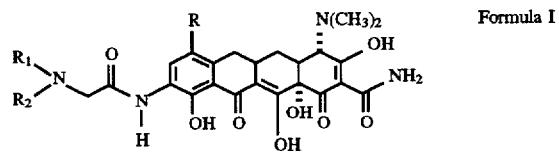

Formula I from its undesired C-4 epimer:

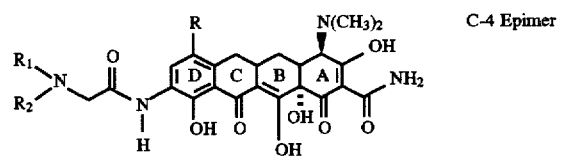

C-4 Epimer by the use of methylene chloride, which method has been heretofore unknown.

Epimerization, at the C-4 position, of the compound of Formula I can occur at every step of each reaction utilized to produce such compound. For example, the C-4 epimerization can occur under mildly acidic conditions, pH below 4, and at temperatures slightly above 25° C. In addition, the presence of moisture in the reaction coupled with low pH and temperatures slightly above 25° C. can rapidly increase the rate of epimerization. The amount of C-4 epimer formed can vary from about 3% to 50% depending on the conditions of the reactions. Thus every stage of each reaction utilized to make the desired 7-(hydrogen or substituted amino)-9-[( (substituted glycyl)amido]-6-demethyl-6-deoxytetracycline must be monitored for C-4 epimer content.

Oxidation at the C-11 and C-12a position of the compound for Formula I can also occur at every step of each reaction uitilized to produce such compound. In addition, when the compound of Formula I contains a 7-disubstituted amino group, the D ring is an aminophenol which is prone to oxidation. The conditions conducive to oxidation are 1) pH greater than 7; 2) the presence of atmosphereic oxygen in solution, (since the compounds of Formula I are more stable in solid form than while in solution) and 3) a combination of increased pH and oxygen. The oxidative degradation by-products have not been characterized. Again, every step of each reaction utilized to make the desired 7-(hydrogen or substituted amino)-9-[(substituted glycyl)amido]-6-demethyl-6-deoxytetracycline must be monitored for oxidative degradation by-products.

The purification method of the present invention is unique to the compounds of Formula I, based on their solubility and the $pK_a$'s of the various ionizable groups. The compounds of Formula I are produced in an aqueous reaction mixture which can also include a combination of organic solvents eg., acetone, dimethylformamide, methyl alcohol, triethylamine, methylene chloride and t-butylamine. Methylene chloride is added to the aqueous reaction mixture at a concentration of 2–4 ml methylene chloride per gram of compound of Formula I and a pH between 6.5–8.0 to extract/dissolve the desired 7-(hydrogen or substituted amino)-9-[(substituted glycyl)amido]-6-demethyl-6-deoxytetracycline compound of Formula I. The undesired C-4 epimer and oxidative degradation by-products, which are not soluble in methylene chloride, remain in the aqueous phase. The methylene chloride extraction procedure of this invention is quick, selective (the undesired C-4 epimer is not soluble in methylene chloride), efficient, and yields very pure desired product, 7-(hydrogen or substituted amino)-9-[(substituted glycyl)amido]-6-demethyl-6-deoxytetracycline. Purity levels of 92–98.5% are obtained. Yields of 26–56% of the compound of Formula I are obtained.

The invention further provides an additional purification, if needed, of 7-(hydrogen or substituted amino)-9-[(substituted glycyl)amido]-6-demethyl-6-deoxytetracycline which comprises the use of a non-ionic reverse phase resin such as Amberchrom®CG161cd, on which the oxidative degradation by-product contaminants adhere. Amberchrom®CG161cd, is a physically strong, macroporous styrenic resin with an exceptionally high surface area (macro-reticular styrene polymeric resin). The Amberchrom®-CG161cd removes about 70% of the oxidative degradation by-products. A subsequent methylene chloride extraction of an Amberchrom®CG161cd wash solution, methyl alcohol/water, is thus cleaner since no emulsions are formed. The resulting concentration in vacuo of the methylene chloride extract gives a purer compound of Formula I, while the contaminants, C-4 epimer and oxidative degradation by-products, remain in the aqueous extract.

DESCRIPTION OF THE PREFERRED EMBODIMENT

Referring to Scheme 1, 7-(hydrogen or substituted amino)-9-nitro-6-demethyl-6-deoxytetracycline or its mineral acid salt, 1a,b, prepared by the procedures of Boothe, J. H. et al, Journal of the American Chemical Society, 82, 1253 (1960); or U.S. Pat. Nos. 3,226,436; 3,518,306 or 5,248,797; is catalytically reduced with hydrogen and a Group VIII metal catalyst in sulfuric acid and methyl alcohol; followed by the addition of hydrochloric acid to the crude reaction mixture, containing the desired 7-(hydrogen or substituted amino)-9-amino-6-demethyl-6-deoxytetracycline and its C-4 epimer, adjusting the pH to between 2–4.5 and isolating 7-(hydrogen or substituted amino)-9-amino-6-demethyl-6-deoxytetracycline, 2a,b, as a crystalline hydrochloride.

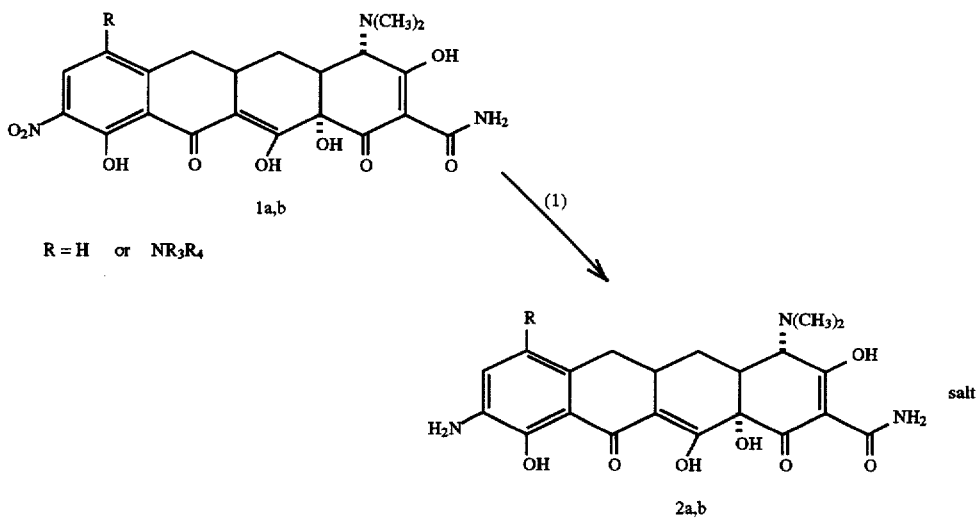

Scheme 2

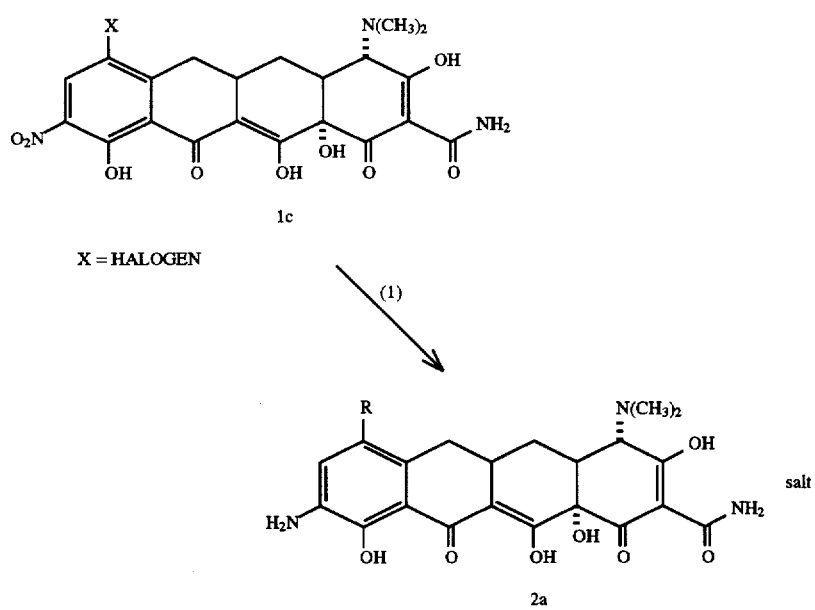

Reagent: (1)=$H_2$; Pd/C

Substitution Legend:
a. R=H
b. R=—$N(CH_3)_2$
c. X=Halogen

Referring to Scheme 2, 7-(halogen)-9-nitro-6-demethyl-6-deoxytetracycline or its mineral acid salt, 1c, prepared by the procedure of U.S. Pat. No. 5,248,797; is catalytically reduced with hydrogen and a Group VIII metal catalyst in sulfuric acid and methyl alcohol; followed by the addition of hydrochloric acid to the crude reaction mixture, containing 9-amino-6-demethyl-6-deoxytetracycline and its C-4 epimer, adjusting the pH to between 1.0–2.0; treating the total crude reaction mixture, which has been suspended in a mixture of 25% methyl alcohol/water, with a non-ionic reverse phase resin such as Amberchrom®CG161cd at a ratio of 3–4 g of washed resin (washed with water; for a moisture content of about 60%), at a pH determined for the specific compound of Formula I; collecting and washing the resin with 25% methyl alcohol/water; adjusting the pH as needed and isolating 9-amino-6-demethyl-6-deoxytetracycline, 2a, as a crystalline hydrochloride;

Scheme 3

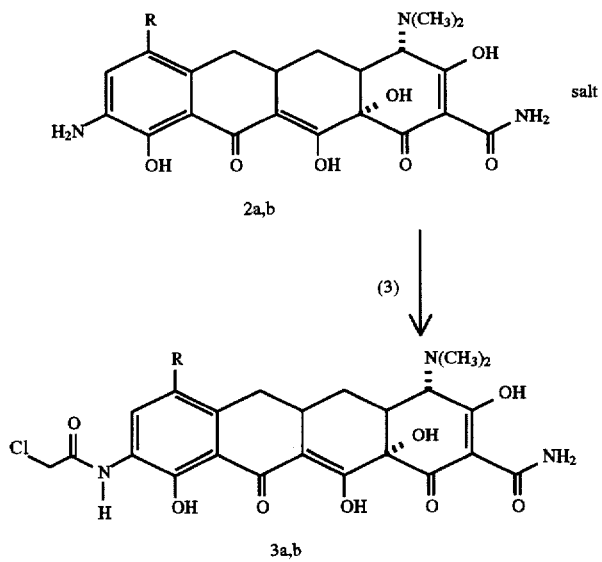

-continued
Scheme 3

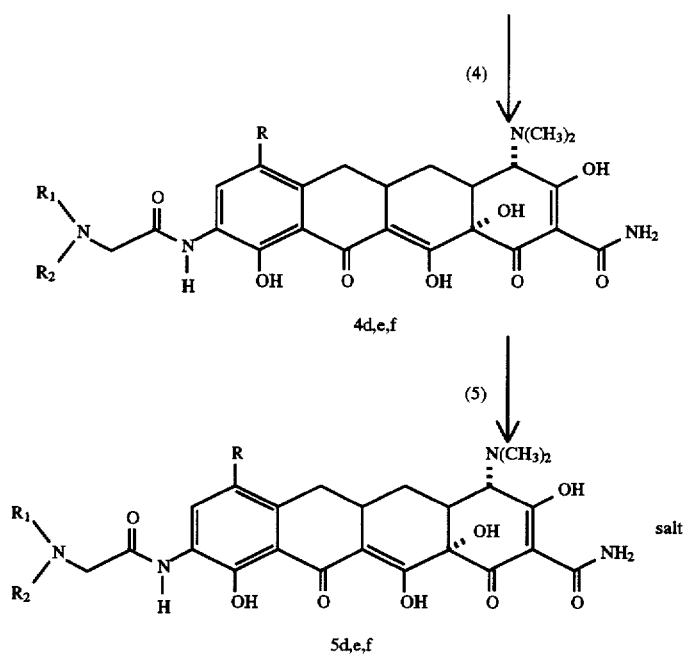

Substitution Legend:

a. R=H
b. R=—N(CH$_3$)$_2$
d. R=H; R$_1$=R$_2$=H
e. R=—N(CH$_3$)$_2$; R$_1$ =R$_2$ =CH$_3$
f. R=—N(CH$_3$)$_2$; R$_1$ =H; R$_2$=t-butyl Reagents:

2. Chloroacetic Anhydride
3. Amine/water
4. Hydrochloric Acid

Referring to Scheme 3, when R=H or —NR$_3$R$_4$, 7-(hydrogen or substituted amino)-9-amino-6-demethyl-6-deoxytetracycline hydrochloride, 2a or 2b, is reacted with chloroacetic anhydride to obtain 7-(hydrogen or substituted amino)-9-[(chloroacetyl)-amino]-6-demethyl-6-deoxytetracycline, 3a or 3b plus the undesired C-4 epimer; the above reaction product mixture is then dissolved, in water and methyl alcohol, and reacted with an amine of the formula H$_2$NR$_1$R$_2$, wherein R$_1$ and R$_2$ are as defined hereinabove, at 0°–5° C. The pH is adjusted at completion of the reaction to between 3–4.5; the reaction mixture contains 4d, 4e, 4f, oxidative degradation by-products formed due to the high pH of the reaction medium and the undesired C-4 epimer. The crude reaction residue (containing 4d, 4e, 4f, oxidative degradation by-products and the undesired C-4 epimer) which has been suspended in a mixture of 25% methyl alcohol/water, at pH 3.0–4.5, is treated with a non-ionic reverse phase resin such as Amberchrom®CG161cd; at a ratio of 3–4 g of washed resin (washed with water; for a moisture content of about 60%); collecting and washing the resin with 25% methyl alcohol/water; adjusting the pH as needed to between 7.0–8.5; and extracting the mixture which contains 4d, 4e, or 4f and traces of undesired C-4 epimer, with methylene chloride. The organic layer is dried with sodium sulfate, the drying agent is filtered off, the solution is treated with activated charcoal, and passed through a pad of diatomaceous earth. The clarified methylene chloride solution is concentrated in vacuo to give the desired 7-(hydrogen or substituted amino)-9-[[(substituted glycyl)amido]-6-demethyl-6-deoxytetracycline, 4d, 4e, or 4f, in high purity. The undesired C-4 epimer is not soluble in the methylene chloride and thus remains in the aqueous phase.

When the reactants are 4d, wherein R=H and R$_1$=R$_2$=H, or 4e, wherein R=—N(CH3)$_2$ and R$_1$=R$_2$=CH$_3$, plus the undesired C-4 epimer, the reaction mixture can be extracted with methylene chloride at a pH between 7.0–8.5, without previously being treated with a non-ionoic reverse phase resin. The methylene chloride solution is dried with sodium sulfate, filtered to remove the drying agent and the organic layer is concentrated in vacuo to give the desired 7-(hydrogen or substituted amino)-9-[[(substituted glycyl) amido]-6-demethyl-6-deoxytetra-cycline, 4d or 4e in high purity. The undesired C-4 epimer is not soluble in the methylene chloride and thus remains in the aqueous phase.

When the reactant is 4f, wherein R$_2$=t-butyl, plus the undesired C-4 epimer, the purification of the reaction mixture, at a pH between 3.0–4.5, requires the use of a non-ionic reverse phase resin such as Amberchrom®CG161cd at a ratio of 7–8 g resin/1 g of crude product and 25% methyl alcohol is the wash; followed by adjusting the pH to between 7.0–8.5 and extracting the mixture with methylene chloride to obtain the desired product, 4f, in high purity. The use of Amberchrom®CG161cd is required in this instance because the oxidative degradation by-products cause heavy emulsion formation during the methylene chloride extraction.

The pure extracted 7-(hydrogen or substituted amino)-9-[(substituted glycyl)amido]-6-demethyl-6-deoxytetracycline, 4d, 4e, or 4f, is treated with an acid as defined hereinbefore, such as hydrochloric acid, to give 7-(substituted amino)-9-[[(substituted glycyl)-amido-6-demethyl-6-deoxytetracycline, 5d, 5e, or 5f, as the salt in this case the hydrochloride salt.

In the present invention, we found that methylene chloride, a water immiscible organic solvent, selectively dissolved the compounds of Formula I while leaving behind the undesired contaminants, the oxidative by-products and the C-4 epimer. Extraction of the crude reaction mixture was attempted with other organic solvents such as isopropyl acetate, methyl isobutylketone (MIBK) and ethyl acetate and the results are presented in Table 1. For example, using isopropyl acetate as the extracting solvent gave only 10% yield of impure desired product. The HPLC indicated approximately 50% of the C-4 isomer present in the extraction solution. Chloroform may not be used in large scale productions due to its toxicity and also the possibility of phosgene formation.

TABLE 1

COMPARISON OF SOLVENTS ON EXTRACTION AND PURITY OF PRODUCT

| EXAMPLE NO. | SOLVENT | % YIELD OF PRODUCT as free base | % OF C-4 ISOMER | PURITY by HPLC % AREA |
| --- | --- | --- | --- | --- |
| 4 | Methylene Chloride | 56.3 | 1.4 | 98.6 |
| 4' | Methylene Chloride | 71.0 | 2.2 | 94.2 |
| 8 | Methylene chloride | 26 | 1.5 | 98.5 |
| 10 | Methylene chloride | 53 | 1.8 | 89–92 |
| 11 | Methyl isobutyl-ketone | <1 | ND | ND |
| 12 | Ethyl acetate | 0 | — | — |
| 13 | Isopropyl Acetate | 10% | 50% | ND |

ND = Not determined

The following non-limiting examples illustrate the method of the present invention.

EXAMPLE 1

9-Amino-4β-dimethylamino-1,2,3,4,4a,5,5a,6,11, 11a,12,12aα-dodecahydro-10,12aα-dihydroxy-1,3, 11,12-tetraoxo-2-naphthacenecarboxamide hydrochloride (9-Amino-6-demethyl-6-deoxytetracycline)

Monohydrocloride

To ten grams of 9-nitro-6-demethyl-6-deoxytetracycline, prepared by the procedure of Boothe, J. H. et al, Journal of the American Chemical Society, 82,1253 (1960) or U.S. Pat. No. 5,248,797, slurried in 100 ml of methyl alcohol is added 40 ml of 2N sulfuric acid followed by 3.3 g of 50% wet palladium on carbon. The mixture is hydrogenated in a Parr apparatus at room temperature and 40 psi of hydrogen. The reaction is filtered through a pad of diatomaceous earth, rinsed 3 times with 10 ml of methyl alcohol and cooled to 10°–15° C. Ten ml of concentrated hydrochloric acid is added to the cooled solution and the pH is adjusted to pH 3.0 with 25% sodium hydroxide. The reaction mixture is allowed to stand at 15° C. for 3 hours (final pH 2.8). The crystalline product is collected, washed with water and methyl alcohol, and dried in vacuo to give 7.0 g of the desired product as the hydrochloride.
Purity by HPLC area % 93.9.

EXAMPLE 2

9-Amino-4β-dimethylamino-1,2,3,4,4a,5,5a,6,11, 11a,12,12α-dodecahydro,10,12aα-dihydroxy-1,3,11, 12-tetraoxo-2-naphthacenecarboxamide hydrochloride (9-Amino-6-demethyl-6-deoxytetracycline)

Monohydrochloride

To 10 g of 7-bromo-9-nitro-6-demethyl-6-deoxytetracycline slurried in 50 ml of methyl alcohol containing 7 ml of triethylamine followed by 3.3 g of 50% wet palladium on carbon. The reaction mixture is hydrogenated at room temperature under 45 psi of hydrogen for 2.75 hours. The solution is filtered through a pad of diatomaceous earth, washed 3× with 10 ml of methyl alcohol. The filtrate volume is adjusted to 200 ml with water, 20 g of sodium chloride is added, and the pH is adjusted to 7.0 with concentrated hydrochloric acid. After adding 0.50 g of sodium sulfite and cooling to 0°–5° C., the reaction mixture is stirred for 15 minutes. The solid is collected and dried to give 7.2 g of the crude product.

The above solid, 7.2 g, is suspended in a mixture of 18 ml of methyl alcohol and 72 ml of water. The pH is adjusted to pH 1.3 with concentrated hydrochloric acid. The mixture is stirred at room temperature for 0.5 hour and filtered. To the clear filtrate is added 27 g of washed Amberchrom®CG161cd, the mixture is stirred for 10 minutes and the resin is collected. The pH of the filtrate is adjusted with concentrated sodium hydroxide to pH 3.0±0.2, stirred at room temperature for 1 hour and allowed to stand at room temperature for an additional hour. The crystals are collected, washed with 5 ml of 15% methyl alcohol/water, and dried at 40° C. in vacuo to give 2.6 g of the desired product.
Purity by HPLC area % 96.5 and C-4 epimer<1%.

EXAMPLE 3

[4S-(4alpha,12aalpha)]-9-[(Chloroacetyl)amino-4-(dimethylamino)-1,4,4a,5,5a,6,11,12a-octahydro-3, 10,12,12a-tetrahydroxy-1,11-dioxo-2-naphthacenecarboxamide Two and a half grams of 9-amino-6-demethyl-6-deoxytetracycline hydrochloride is added in portions, at 15°–20° C., to a solution of 17 ml of dimethylformamide and 0.6 ml of concentrated sulfuric acid. The added solid is completely in solution after 15 minutes. The solution is then cooled to 0° C. and 2.3 g of chloroacetic anhydride in 5 ml of dimethylformamide is added, dropwise, while maintaining the temperature at 0°–2° C. The reaction mixture is stirred for 30 minutes, poured into 40 g of ice and 35 ml of water, and the pH is adjusted to pH 5.34 with concentrated ammonium hydroxide. The resulting solid is stirred for 30 minutes, collected, washed 2× with water, washed 2× acetone and dried in vacuo to give 2.4 g of the desired intermediate.
Purity by HPLC area % 83.

EXAMPLE 4

[4S-(4alpha,12aalpha)]-4-(Dimethylamino)-9-[[ (dimethylamino)acetyl]amino]-1,4,4a,5,5a,6,11,12a-octahydro-3,10,12,12a-tetrahydroxy-1,11-dioxo-2-naphthacenecarboxamide Ten grams of 9-chloroamide-6-demethyl-6-deoxytetracycline, product from Example 3, is suspended in 50.1 ml of water and 4.9 ml of methyl alcohol and cooled to 0°–5° C. Fifty and one tenth ml (50.1 ml) of dimethylamine is added and the reaction is stirred at 0°–5° C. for 0.5 hour followed by 0.5 hour at room temperature. The mixture is re-cooled, the pH is adjusted with concentrated hydrochloric acid to pH 3.0. Amberchrom®CG161cd resin (1.57 g dry resin/1 g of compound) is added and the slurry is stirred for 15 minutes. The resin is collected and the filtrate (A) is saved. The compound is stripped off the resin using 55% methyl alcohol/water. The methyl alcohol eluate and filtrate (A) are combined, extracted with methylene chloride at pH 8.5 and concentrated in vacuo. The residue is recrystallized from methylene chloride/heptane to give 4.0 g (56.3% yield) of the desired product.

Purity by HPLC area % 98.6 and C-4 epimer 1.4%.

EXAMPLE 4' (LARGE SCALE)

[4S-(4alpha,12aalpha)]-4-(Dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide monohydrochloride Six hundred and seventy-five g of 9-chloro-amide-6-demethyl-6-deoxytetracycline, made by the procedure of Example 3, is suspended in 3.38 L of water and 169 ml of methyl alcohol and cooled to 0°–5° C. To this cooled solution is added 3.38 L of dimethylamine while maintaining the temperature at 0°–5° C. The reaction mixture is stirred at 0°–5° C. for 30 minutes after the completion of the addition and then at room temperature for 30–60 minutes.

The reaction mixture is cooled to 0° C. and the pH adjusted to 7.5–7.6 with concentrated hydrochloric acid. The temperature is allowed to rise to room temperature and the pH is adjusted to 7.5–7.6 if necessary. The reaction mixture is extracted with 8×5 L of methylene chloride; adjusting the pH to 7.5–7.6 before every extraction.

The methylene chloride layer is dried, concentrated in vacuo to about 2.5 L and 2.5 L of isopropyl alcohol and 17 L of heptane are added. The light yellow precipitate is collected to give 487 g (71% yield) of [4S-(4alpha,12aalpha)]-4-(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide as the free base.

Purity by HPLC area % 94.19 and C-4 epimer 2.2%.

To 480 g of the above free base, suspended in 1920 ml of chilled (−5° C.–10° C.) methyl alcohol is added a calculated quantity of methanolic hydrogen chloride (32.38 g HCl). As the addition proceeds the free base gradually dissolves in the solution. After 15–20 minutes the hydrochloric gradually crystallizes out of the solution. After 1.5 hours, 1920 ml of isopropyl alcohol is added to aid the precipitation of the product. The solid is collected, washed with 500 ml of isopropyl alcohol and dried in vacuo at 40° C. to give 495 g of the desired product (yield 96% of theory).

Analysis calculated for $C_{25}H_{30}N_4O_8 \cdot HCl \cdot H_2O$ Theory: C=52.77; H=5.45; N=9.85; Cl=6.24 Found: C=52.84; H=5.85; N=9.74; Cl=5.80

EXAMPLE 5

Purification of [4S-(4alpha,12aalpha)]-9-Amino-4,7-bis(dimethylamino)-1,4,4a,5,5a,6,11,12a-octahydro-3,10,12,12a-tetrahydroxy-1,11-dioxo-2-naphthacenecarboxamide sulfate by Conversi Four hundred grams of crude 9-amino-7-di-methylamino-6-demethyl-6-deoxytetracycline sulfate, prepared by the procedure of U.S. Pat. No. 5,248,797, contaminated with 11.5% of the C-4 epimer, is added slowly to 672 ml of deionized water, cooled in an acetone/dry ice bath, and stirred until complete solution occurred (internal temperature 3° C.). Eighty one ml of concentrated hydrochloric acid is added slowly maintaining the temperature at 0°–10° C. (pH 0.83–1.0, after addition is complete). The stirring is continued for an additional 5 minutes, followed by the careful addition of 245 ml of concentrated ammonium hydroxide to bring the pH to 4.0 while maintaining the temperature at 0°–5° C. Sodium sulfite, 0.708 g, is added along with 1.3 g of pure 9-amino-7-dimethylamino-6-demethyl-6-deoxytetracycline as seed crystals. The solution is maintained at 0°–10° C., the pH is monitored and kept at 4.0±0.2, for 1 hour and then the solution is maintained at 4° C. for 16 hours. The solid is collected, washed with 220 ml of pH 4.0 water, and dried in vacuo at 40° C. to give 172 g of 9-amino-7-dimethylamino-6-demethyl-6-deoxytetracycline hydrochloride containing 3.5% epimer content.

Purity by HPLC area % 96.0. MS(FAB): m/z 473 (M+H), 472 (M$^+$).

EXAMPLE 6

Recrystallization of 9-Amino-4,7-bis(dimethylamino)-1,4,4a,5,5a,6,11,12a-octahydro-3,10,12,12a-tetrahydroxy-1,11-dioxo-2-naphthacenecarboxamide Monohydrochloride To 2.3 L of deionized water is added, slowly with stirring, 1.62 Kg of 9-amino-7-dimethyl-6-demethyl-6-deoxytetracycline, C-4 epimer content 3.5%. Concentrated hydrochloric acid, 410 ml, is added slowly maintaining the temperature at 10°–15° C. (final pH 1.2). After complete dissolution of the solid amine, 55 g of washed charcoal is added, the suspension is stirred an additional 15–20 minutes and the mixture is filtered through a pad of pre-washed diatomaceous earth. The pad is washed with 400 ml of deionized water. The filtrate and wash are combined and cooled to 0°–5° C. in a dry ice/acetone bath. Concentrated ammonium hydroxide, 320 ml, is added dropwise maintaining the temperature at 0°–5° C. (pH 4.01). The resulting slurry is stirred until the pH is stabilized at 4.0±0.2 and then stored in a refrigerator at 4° C. for 20 hours. The precipitate is collected, washed with cold deionized water, pH 4.0, and dried in vacuo at 40° C. to give 1.43 Kg of the desired product.

Purity by HPLC % area 97.0 and C-4 epimer 2.9%. Analysis calculated for $C_{23}H_{28}N_4O_7 \cdot HCl \cdot 3H_2O$ Theory: C=54.27; H=5.70; N=11.0; Cl=6.98 Found: C=54.34; H=5.53; N=10.9; Cl=7.08 MS(FAB): m/z 473 (M+H).

EXAMPLE 7

[4S-(4alpha,12aalpha)]-9-[(Chloroacetyl)amino]4,7-bis(dimethylamino)-1,4,4a,5,5a,6,11,12a-octahydro-3,10,12,12a-tetrahydroxy-1,11-dioxo-2-naphthacenecarboxamide Methylene chloride, 1.32 L, is cooled in a 3-neck round bottom flask fitted with a mechanical stirrer and a thermometer. Four hundred grams of 9-amino-7-dimethylamino-6-demethyl-6-deoxytetracycline is added in portions while maintaining the temperature at 0°–2° C. followed by the addition of 428 ml of triethylamine. The reaction is stirred for 10 minutes following the addition of triethylamine. The solution mixture is cooled to −25° C. and a solution of 280 g of chloroacetic anhydride in 540 ml of methylene chloride is added at such a rate that the temperature is maintained between 0°–2° C. The addition funnel is rinsed with 132 ml of methylene chloride. The reaction progress is monitored by HPLC for the disappearance of starting amine. Total Reaction Time=40 minutes from start of addition. The reaction is quenched with 680 ml of 0.5N sodium bicarbonate and then stirred for 15 minutes. The organic layers are separated and the methylene chloride layer is washed with an additional 680 ml of 0.5N sodium bicarbonate followed by the rapid addition of the solution, with stirring, to a solution of 10:1 heptane:isopropanol. The supernatant is decanted, the suspension is filtered, washed with 2 L of 10:1 heptane:isopropanol and dried in vacuo overnight to give 465 g of the product as a mixture of esters which are used without further purification. The hydrolysis of the esters occurs in the next step.

EXAMPLE 8

[4S-(4alpha,12aalpha)]4,7-Bis(dimethylamino)-9-[[(t-butylamino)acetyl]amino]-1,4,4a,5,5a,6,11,12a-octahydro-3,10,12,12a-tetrahydroxy-1,11-dioxo-2-naphthacenecarboxamide Monohydrochloride To 125 ml of t-butylamine, under argon, is added portionwise 25 g of product from Example 7, while maintaining the temperature at 25°–30° C., followed by the addition of 2.5 g of sodium iodide. The mixture is stirred at room temperature for 5.5 hours. The reaction progress is monitored by HPLC. To the reaction is added 25 ml of methyl alcohol and the organic solvents are removed in vacuo. To the resulting residue is added 105 ml of methyl alcohol and 170 ml of water, the mixture is cooled to 0°–2° C. and the pH is adjusted to pH 7.2–7.4 with concentrated hydrochloric acid. The solution is stirred in a chill room at 8° C. overnight. The HPLC assay indicates complete hydrolysis. Total volume is 335 ml. The volume is adjusted to 2.9 L with water and the pH is adjusted to 4.0–4.2 with concentrated hydrochloric acid. Wet Amberchrom®CG161cd, 216 g, is added to the solution and the solution is stirred for 30 minutes at room temperature after adjusting the pH to 4.0 with concentrated ammonium hydroxide. The suspension is filtered and the eluate saved (Eluate 1). The resin is re-slurried with 1.2 L of 20% methyl alcohol/water and the pH is adjusted to pH 4.0 as needed. The slurry is stirred for 20 minutes and filtered saving the eluate (Eluate 2). This process is repeated 2× more, washing each time with 1.2 L of 20% methyl alcohol/water (Eluates 3 and 4). Prior to each washing with 20% methyl alcohol/water, the pH is adjusted to 4.0–4.2. The eluates, 1–4, are combined and the pH is adjusted to pH 7.2–7.3 with ammonium hydroxide. The solution is extracted 5× with 700 ml of methylene chloride stirring for 10 minutes and adjusting the pH to pH 7.2–7.3 before each extraction. The methylene chloride extracts are combined and concentrated in vacuo to dryness. The residue is stirred vigorously with 45 ml of cold methylene chloride. The precipitate is collected, washed 2× with cold methylene chloride and dried at 40° C. in vacuo to give 6.6 g of the free base (yield 26% of theory).
Purity by HPLC area % 96.6 and C-4 epimer 1.5%. MS(FAB): m/z 586 (M+H); 585 (M$^+$).

EXAMPLE 9

Formation and Lyophilization of [4S-(4alpha,12aalpha)]-4,7-Bis(dimethylamino)-9-[[(t-butylamino)acetyl]amino]-1,4,4a,5,5a,6,11,12a-octahydro-3,10,12,12a-tetrahydroxy-1,11-dioxo-2-naphthacenecarboxamide Monohydrochloride To 3.0 grams of product from Example 8 dissolved in 60 ml of water, cooled to 0° C., Initial pH 8.25, is added 410 μl of concentrated hydrochloric acid, Final pH 6.5. The solution is lyophilized at 4° C. for 72 hours followed by 21° C. for 2 hours.
Product Yield=2.9 g Analysis calculated for $C_{29}H_{39}N_5O_8 \cdot HCl \cdot 2H_2O$: C=52.92; H=6.60; N=10.65; Cl=5.4
Found: C=52.64; H=6.99; N=10.57; Cl=4.97 (Total) Cl=5.10 (Ionic)
Purity by HPLC area % 98.0 and C-4 epimer 1.04%. MS(FAB):m/z 586 (M+H) and 585 (M$^+$).

EXAMPLE 10

[4S-(4alpha,12aalpha)]-4,7-Bis(dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide Monohydrochloride To a room temperature mixture of 1.45 L of methyl alcohol and 969 ml of water, in a 12 L 3-neck round bottom flask fitted with a mechanical stirrer and thermometer, is added in portions 346 g of product from Example 7. The mixture is stirred for 90 minutes, followed by the addition of 1.4 L of dimethylamine while maintaining the temperature below 25° C. The reaction is stirred for 0.5 to 1 hour, monitored by HPLC. The mixture is cooled to −5° C. (internal temperature) and 1.4 L of cold water is added. Concentrated hydrochloric acid, 810 ml, is added maintaining the temperature at 15°–18° C. When the pH is 7.0–7.2, the solution is transferred and extracted with 1.4 L of methylene chloride. This process is repeated 4× using 1.4 L of methylene chloride each time and adjusting the pH of the aqueous phase prior to extraction to pH 7.0–7.2. The methylene chloride extracts are combined, 31 g of charcoal is added and the mixture is stirred at room temperature for 10 minutes. The carbon slurry is passed through a pad of diatomaceous earth, the pad is rinsed with 925 ml of methylene chloride, dried and concentrated in vacuo to give 176 g of the desired free base (yield 53% of theory).
Purity by HPLC area % 89–92 and C-4 epimer 1.8%. MS(FAB):m/z 557(M$^+$).

To 485 ml of water containing 24.25 g of sodium chloride is added with stirring 171 g of the above free base. After the solid is completly dissolved, the solution is filtered and the funnel washed with 370 ml of 5% sodium chloride solution. The solution is cooled to 0°–2° C. (acetone/dry ice) and 23 ml of concentrated hydrochloric acid is added dropwise with stirring. The pH at the start of addition is pH 7.81 and the final pH is 6.98. Crystals form and the stirring is continued for 15 minutes. The crystalline slurry is filtered through polypropylene paper on a table top filter funnel. The solid cake is washed with 2×375 ml of cold 1% sodium chloride solution, followed by 2×600 ml of cold acetone. The solid is slurried in 600 ml of cold acetone, stirred for 10 minutes, collected on a polypropylene paper on a table top filter funnel and washed with 500 ml of cold acetone. The crystalline material is dried at 35° C. in vacuo for 24 hours to give 304 g of the desired product as the hydrochloride.
Purity by HPLC area % 97.8 and C-4 epimer 2.5%. MS(FAB):m/z 558 (M+H) and 557 (M$^+$).

EXAMPLE 11

[4S-(4alpha,12aalpha)]-4-(Dimethylamino)-9-[[(dimethylamino)acetyl]amino]-1,4,4a,5,5a,6,11,12a-octahydro-3,10,12,12a-tetrahydroxy-1,11-dioxo-2-naphthacenecarboxamide (Methyl isobutylketone Extraction)

The title compound is prepared by the procedure of Example 4' using 10 g of 9-chloro-amide-6-demethyl-6- deoxytetracycline, 50 ml of water, 50 ml of dimethylamine, 6 ml of concentrated ammonium hydroxide, and 32 ml of concentrated hydrochloric acid. Three×100 ml of methyl isobutylketone is used in the extraction to give 0.10 g of product (yield<1% of theory).

EXAMPLE 12

4-(Dimethylamino)-9-[[(dimethylamino)acetyl]
amino]-1,4,4a,5,5a,6,11,12a-octahydro-3,10,12,12a-
tetrahydroxy-1,11-dioxo-2-naphthacenecarboxamide (Ethyl Acetate Extraction)

The title compound is prepared by the procedure of Example 4' using 10 g of 9-chloro-amide-6-demethyl-6-deoxytetracycline, 50 ml of water, 50 ml of dimethylamine, 6 ml of concentrated ammonium hydroxide, and 32 ml of concentrated hydrochloric acid. Three×100 ml of ethyl acetate is used in the extraction to give 0.0 g the desired product.

EXAMPLE 13

4-(Dimethylamino)-9-[[(dimethylamino)acetyl]
amino]-1,4,4a,5,5a,6,11,12a-octahydro-3,10,12,12a-
tetrahydroxy-1,11-dioxo-2-naphthacenecarboxamide The title compound is prepared by the procedure of Example 4' using 10 g of 9-chloro-amide-6-demethyl-6-deoxytetracycline, 50 ml of water, 50 ml of dimethylamine, 6 ml of concentrated ammonium hydroxide, and 32 ml of concentrated hydrochloric. Three×100 ml of isopropyl acetate is used in the extraction to give less than 10% the desired product. The extracted material was impure, 50% of C-4 isomer.

We claim:

1. A method for selectively extracting a compound of formula I:

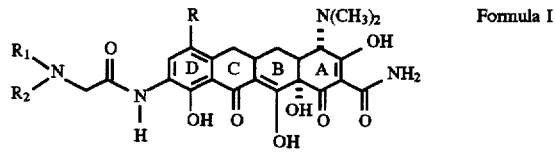

wherein: R is hydrogen or —NR$_3$R$_4$; and when R=—NR$_3$R$_4$, R$_3$ and R$_4$ may be the same or different and are selected from hydrogen and straight or branched (C$_1$–C$_4$)alkyl; R$_1$ and R$_2$ may be the same or different and are selected from hydrogen and methyl; from an aqueous mixture comprising the compound of Formula I, its C-4 epimer and its oxidative by-products which method comprises adding methylene chloride to the aqueous mixture at a concentration of 2–4 ml of methylene chloride per gram of compound of Formula I and at a pH between pH 6.5–8.0; and obtaining an extract consisting essentially of methylene chloride, the compound of Formula I, and its C-4 epimer, said epimer being present in an amount less than 3% of the amount of the compound of Formula I, said amount as measured by HPLC area percent.

2. The method of claim 1 which further comprises reacting the methylene chloride extract with an acid to form an acid salt of the compound of Formula 1.

3. The method of claim 2 wherein the acid is selected from hydrochloric, hydrobromic, hydroiodide, phosphoric, nitric, sulfuric, acetic, benzoic, citric, cystein, fumaric, glycolic, maleaic, succinic, tartaric, alkylsulfonic and arylsulfonic acid.

4. The method of claim 3 wherein the acid is hydrochloric acid.

5. The method of claim 1 wherein the pH range is 7.0–7.4.

6. The method of claim 1 wherein the extraction is carried out at a temperature of 10°–35° C.

7. The method of claim 1 wherein said extract is further treated with charcoal and filtered through diatomaceous earth.

8. The method of claim 1 wherein the concentration of methylene chloride/compound of Formula 1 is 3–4 ml of methylene chloride/1 g of compound of Formula I.

9. The method of claim 1 wherein the aqueous mixture is treated with a non-ionic reverse phase resin at a pH range of 3.0 to 5.0 prior to extraction with methylene chloride.

10. The method of claim 9 wherein the reverse phase resin is a macro-reticular styrene polymeric resin.

11. The method of claim 2 wherein the compound of formula I is -4,7-bis(dimethylamino)-9-[[(dimethylamino) acetyl]amino]-1,4,4a,5,5a,6,11,12a-octahydro-3,10,12,12a-tetrahydroxy-1,11-dioxo-2-naphthacenecarboxamide mono-hydrochloride.

12. The method of claim 2 wherein the compound of formula I is 4-(dimethylamino)-9-[[(dimethylamino)acetyl] amino]-1,4,4a,5,5a,6,11,12a-octahydro-3,10,12,12a-tetrahydroxy-1,11-dioxo-2-naphthacenecarboxamide mono-hydrochloride.

13. A method for selectively extracting a compound of formula I:

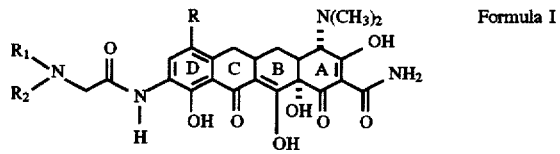

wherein: R is hydrogen or —NR$_3$R$_4$; and when R=—NR$_3$R$_4$, R$_3$ and R$_4$ may be the same or different and are selected from hydrogen and straight or branched (C$_1$–C$_4$)alkyl; R$_1$ and R$_2$ are selected from hydrogen and t-butyl; from an aqueous mixture comprising the compound of Formula I, its C-4 epimer and its oxidative by-products which method comprises treating the aqueous mixture with a non-ionic reverse phase resin at a pH range of 3.0 to 5.0; adding methylene chloride to the aqueous mixture at a concentration of 2–4 ml of methylene chloride per gram of compound of Formula I and at a pH between pH 6.5–8.0; and obtaining an extract consisting essentially of methylene chloride, the compound of Formula I, and its C-4 epimer, said epimer being present in an amount less than 3% of the amount of the compound of Formula I, said amount as measured by HPLC area percent.

14. The method of claim 13 wherein the compound of formula I is -4,7-bis(dimethylamino)-9-[[(t-butylamino) acetyl]amino]-1,4,4a,5,5a,6,11,12a-octahydro-3,10,12,12a-tetrahydroxy-1,11-dioxo-2-naphthacenocarboxamide dihydrochloride.

* * * * *